United States Patent [19]

Maruta et al.

[11] Patent Number: 4,978,808
[45] Date of Patent: Dec. 18, 1990

[54] METHOD OF PRODUCING 2,2-BIS(3-NITRO-4-HYDROXYPHENYL)-HEXAFLUOROPROPANE

[75] Inventors: Masamichi Maruta, Kawagoe; Tetsuo Wada, Ube, both of Japan

[73] Assignee: Central Glass Company, Limited, Ube, Japan

[21] Appl. No.: 359,229

[22] Filed: May 31, 1989

[30] Foreign Application Priority Data

May 31, 1988 [JP] Japan .................................. 63-131456

[51] Int. Cl.$^5$ .............................................. C07C 79/32
[52] U.S. Cl. .................... 568/707; 568/706; 568/709; 568/713
[58] Field of Search .............. 568/707, 709, 713, 710

[56] References Cited

U.S. PATENT DOCUMENTS 2,615,052 10/1952 Faith .................................. 568/707
4,525,539 6/1985 Feiring .............................. 525/326

OTHER PUBLICATIONS

J. Polymer Science, Polymer Chem. Ed., 20,2381, (1982), pp. 2381–2393.
J. Polymer Science, Polymer Lett., 7,185, (1969), pp. 185–191.

*Primary Examiner*—Werren B. Lone
*Attorney, Agent, or Firm*—Fleit, Jacobson, Cohn, Price, Holman & Stern

[57] ABSTRACT

Disclosed herein is a method of producing 2,2-bis(3-nitro-4-hydroxphenyl)hexafluoropropane, which comprises (a) preparing 2,2-bis(4-hydroxyphenyl)hexafluoropropane and a lower fatty acid; and (b) allowing the 2,2-bis(4-hydroxyphenyl)hexafluoropropane to react with nitric acid in the lower fatty acid.

10 Claims, No Drawings

METHOD OF PRODUCING 2,2-BIS(3-NITRO-4-HYDROXYPHENYL)HEXAFLUOROPROPANE

BACKGROUND OF THE INVENTION

1. Field of the Invention

The present invention relates to a method of producing 2,2-bis(3-nitro-4-hydroxyphenyl)hexafluoropropane which is usable as an intermediate material for 2,2-bis(3-amino-4-hydroxyphenyl)hexafluoropropane or the like.

2. Description of the Prior Art

In order to produce 2,2-bis(3-nitro-4-hydroxyphenyl)hexafluoropropane, two methods have been widely used, one being a method in which, as is shown in Japanese Patent First Provisional Publication No. 59-109546, 2,2-bis(4-hydroxyphenyl)hexafluoropropane is mixed with potassium nitrate in trifluoro acetic acid, and the other being a method in which, as is shown in J.POLYMER SCIENCE, POLYMER CHEM. ED. 20,2381 (1982), 2.2-bis(4-hydroxyphenyl)hexafluoropropane is mixed with trifluoromethane sulfonic acid to form triflate (trifluoromethanesulfonate) and then the triflate is nitrated by mixed acid.

However, in these conventional methods, usage of expensive solvents and agents is needed. Furthermore, purification of product should be effected by means of troublesome distillation.

Furthermore, according to J.Polymer Science, Polymer Lett., 7,185 (1969) in which nitration on 2,2-bis(4-hydroxyphenyl)propane is discussed, it is reported that when 2,2-bis(4-hydroxyphenyl)propane was nitrated by concentrated nitric acid in mixed solvent of benzene-acetic acid, about 38% dinitro-substance was obtained, but, the dinitro-substance exhibited poor purity due to contamination by mononitro-substance and trinitro-substance. The report concluded that preferably, nitration of dichloroformate of 2,2-bis(4-hydroxyphenyl)propane should be made by silver nitrate in acetonitrile. In either case, it is difficult to obtain a highly purified dinitro-substance when using nitric acid.

SUMMARY OF THE INVENTION

It is therefore an object of the present invention to provide a method of producing 2,2-bis(4-hydroxyphenyl)hexafluoropropane, which method exhibits a high yield of the product.

In the method of the present invention, a lower fatty acid having a carbon number of 2 to 5 is used as atmosphere for nitration of 2,2-bis(4-hydroxyphenyl)hexafluoropropane by nitric acid.

According the present invention, there is provided a method of producing 2,2-bis(3-nitro-4-hydroxyphenyl)-hexafluoropropane, which comprises (a) preparing 2,2-bis(4-hydroxyphenyl)hexafluoropropane and a lower fatty acid; and (b) allowing the 2,2-bis(4-hydroxyphenyl)hexafluoropropane to react with nitric acid in the lower fatty acid.

DETAILED DESCRIPTION OF THE INVENTION

In order to discover a method for solving the above-mentioned drawbacks encountered in the conventional methods, the applicants have carried out various examinations and tests and finally discovered the improved method as described hereinabove.

The examinations and tests carried out by the applicants have revealed the important facts which will be summarized in the following.

The lower fatty acid usable in the invention is acetic acid, propionic acid, butyric acid or the like. These acids dissolve very well both the material, viz., 2,2-bis(4-hydroxyphenyl)hexafluoropropane and the intermediate product, viz., mononitro-substance. However, the acids do not dissolve the target dinitro-substance well. Accordingly, it is possible to obtain the target dinitro-substance as a highly purified crystal form.

If a certain amount of water is present in the system of reaction, solubility of the dinitro-substance to the acids is much reduced thereby achieving a higher yield of the crystallized dinitro-substance. However, if water is too much, the mononitro-substance is also deposited as oil matter. Thus, it is necessary to determine the concentration of nitric acid by considering the amount of the fatty acid and the amount of water which will be produced during the reaction.

The amount of the lower fatty acid used for the reaction is so made that 0.8 to 2.0 Kg, preferably, 1.5 to 1.8 Kg, of 2,2-bis(4-hydroxyphenyl)hexafluoropropane is put in 1 liter of the fatty acid.

The amount of the nitric acid used is about 2 to 3 equivalent to the material, viz., 2,2-bis(4-hydroxyphenyl)hexafluoropropane. The nitric acid having a specific gravity of 1.38 to 1.52 is usable.

In order to obtain the target dinitro-substance with high yield and high purity, addition of water into the system of reaction is preferable. For this, the amount of the additional water is 0.01 to 1.5, preferably 0.4 to 0.6 times as much as that of the lower fatty acid used.

The temperature for the reaction should be within a range from about 30° C. to about 70° C. If the temperature is lower than 30° C., sufficient reaction is not obtained, and if the temperature is higher than 70° C., undesired higher order nitration is developed.

The present invention will be further described by the following nonlimitative examples.

EXAMPLE 1

672g (2 mol) of 2,2-bis(4-hydroxyphenyl)hexafluoropropane was disolved in 400 ml of acetic acid at 50° C., then 350 ml (2.3 equivalent) of nitric acid (SPG: 1.38) was added dropwise to the solution taking about 1 hour at 50° C. Deposition of a crystallized substance appeared in the solution when about ⅔ of the nitric acid had been consumed. Thereafter, the solution was left at 50° C. for about 1 hour. Then, for sufficiently depositing the crystallized substance, 270 ml of water was added to the solution while adjusting a slurry concentration. Under this condition, the amount of water in the system of reaction was calculated 518 ml. Yellow crystallized substance thus produced in the solution was filtered and washed with 200 ml of 50% methanol, and then, the substance was dried in an oven. These steps gave 753 g of 2,2-bis(3-nitro-4-hydroxyphenyl) hexafluoropropane with 99.9 % purity in a 88.4% yield. The fusing point of the product was 118° to 121.5° C.

EXAMPLE 2

Substantially the same steps as the above-mentioned example-1 were carried out except that in the example-2, 400 ml (2.63 equivalent) of nitric acid was used. The steps of this example gave 794 g of 2,2-bis(3-nitro-4-hydroxyphenyl) hexafluoropropane with 99.9 % purity in a 93.2 yield. At the time when the reaction was finished, the amount of water in the system of reaction was calculated 557 ml.

EXAMPLES 3, 4, 5 AND 6

Conditions of these examples are depicted by TABLE-1. The reaction was carried out for 2 hours in each example.

TABLE 1

|  | *2,2-bis (4-hydroxy-phenyl (hexafluoro-propane) (g) | solvent (ml) | nitric acid (g) | water in system of reaction (ml) | temperature (°c.) | yield (%) |
| --- | --- | --- | --- | --- | --- | --- |
| Example-3 | 20 | acetic acid 25 | 10 | 7.7 | 40 | 68.8 |
| Example-4 | 40 | acetic acid 30 | 20 | 15.3 | 55 | 81.4 |
| Example-5 | 80 | acetic acid 50 | 40 | 30.6 | 65 | 92.3 |
| Example-6 | 40 | propionic acid 30 | 20 | 15.3 | 50 | 87.0 |

Note
Specific gravity of nitric acid is 1.38. Amount of nitric acid in case of Example-3 is 2.21 equivalent to the material*, while amount of nitric acid in cases of Examples-4 to 6 is 2.24 equivalent to the material*. The amount of water in the system of reaction is a calculated value assumed when the reaction is finished.

What is claimed is:

1. A method of producing 2,2-bis(3-nitro-4-hydroxyphenyl)hexafluoropropane, comprising the step of:
    reacting 2,2 bis(4-hydroxyphenyl)hexafluoropropane with nitric acid in a lower fatty acid at a temperature within a range from about 30° C. to about 70° C.

2. A method as claimed in claim 1, in which said lower fatty acid has the carbon number of 2, 3, 4 or 5.

3. A method as claimed in claim 1, further comprising the step of:
    adding water into the system of reaction.

4. A method as claimed in claim 3, in which said lower fatty acid is one of the group consisting of acetic acid, propionic acid and butyric acid.

5. A method as claimed in claim 4, in which the amount of the lower fatty acid is so selected that 0.8 to 2.0 Kg of 2,2-bis(4-hydroxyphenyl)hexafluoropropane is put in 1 liter of the fatty acid.

6. A method as claimed in claim 5, in which the amount of the lower fatty acid is so selected that 1.5 to 1.8 Kg of 2,2-bis(4-hydroxyphenyl)hexafluoropropane is put in 1 liter of the fatty acid.

7. A method as claimed in claim 6, in which the amount of the nitric acid is approximately 2 to 3 equivalent to 2,2-bis(4-hydroxyphenyl)hexafluoropropane.

8. A method as claimed in claim 7, in which the nitric acid used has a specific gravity of approximately 1.38 to 1.52.

9. A method as claimed in claim 3, in which the amount of water to be added to the reaction system is approximately 0.01 to 1.5 times as much as that of the lower fatty acid used.

10. A method as claimed in claim 9, in which the amount of water to be added to the reaction system is approximately 0.4 to 0.6 times as much as that of the lower fatty acid used.

* * * * *